United States Patent
Long et al.

(10) Patent No.: US 6,479,015 B1
(45) Date of Patent: *Nov. 12, 2002

(54) APPARATUS FOR MONITORING A LEVEL OF A CHEMICAL SPECIES IN A BODY FLUID

(75) Inventors: Nathan R. Long, Ada, MI (US); Eric A. Peper, Lincoln, NE (US); James L. Say, Alameda, CA (US); Mark S. Vreeke, Alameda, CA (US)

(73) Assignee: Pepex Biomedical, LLC, Villa Park, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/033,767
(22) Filed: Mar. 3, 1998
(51) Int. Cl.[7] .............................................. G01N 33/48
(52) U.S. Cl. ........................... 422/58; 422/61; 436/166; 436/174; 436/811; 600/309; 600/346; 600/362
(58) Field of Search ................................ 436/169, 811, 436/174, 166, 177; 422/56, 58, 61; 600/306, 309, 346, 362

(56) References Cited

U.S. PATENT DOCUMENTS

| | | |
|---|---|---|
| 3,461,036 A | 8/1969 | Harvill et al. |
| 3,986,494 A | 10/1976 | Preti et al. |
| RE30,267 E * | 5/1980 | Bruschi ......................... 422/56 |
| 4,457,748 A | 7/1984 | Lattin et al. |
| 4,458,686 A | 7/1984 | Clark, Jr. |
| 4,756,314 A | 7/1988 | Eckenhoff et al. |
| 4,819,645 A | 4/1989 | Peck |
| 4,821,733 A | 4/1989 | Peck |
| 4,846,182 A | 7/1989 | Fogt et al. |
| 4,897,347 A * | 1/1990 | Katsuyama et al. ........... 422/56 |
| 5,050,604 A | 9/1991 | Reshef et al. |
| 5,076,273 A | 12/1991 | Schoendorfer et al. |
| 5,234,813 A * | 8/1993 | McGeehan et al. ............ 422/56 |

(List continued on next page.)

FOREIGN PATENT DOCUMENTS

| | | |
|---|---|---|
| DE | 208 675 | 4/1984 |
| EP | 0 895 084 A2 | 2/1999 |
| JP | 04-28343 | 1/1992 |
| WO | WO 94/14062 | 6/1994 |
| WO | WO 98/37424 | 8/1998 |

OTHER PUBLICATIONS

Faridnia, M. H., Abstract of "Amperometric Biosensors for Metabolite Determination in Body Fluids," Dissertation, University of New Orleans (1991).
Faridnia, M. H. et al., Abstract of "Amperometric Biosensor for Determination of Lactate in Sweat," *Anal. Chem. Acta* 278, 35–40 (1993).
Guilbault, G. et al., "Non–invasive biosensors in clinical analysis," *Biosensors & Bioelectronics,* 10:379–392 (1995).

*Primary Examiner*—Lyle A. Alexander
(74) *Attorney, Agent, or Firm*—Merchant & Gould P.C.

(57) ABSTRACT

An apparatus for monitoring a level of a chemical species in a body fluid includes a fluid collection layer adapted for receiving the body fluid. The fluid collection layer is dry prior to being brought into contact with the body fluid. A catalyst is provided in, on, or near the fluid collection layer so as to be in contact with the body fluid in the fluid collection layer. The catalyst facilitates a reaction of the chemical species in the body fluid. An indicator, responsive to the reaction of the chemical species, is also provided in, on, or near the fluid collection layer. A characteristic of the indicator changes in response to the reaction of the chemical species, thereby indicating the level of the chemical species in the body fluid. This apparatus can be used, for example, to monitor the level of lactate in perspiration during activities, such as exercise or other athletic exertions.

43 Claims, 3 Drawing Sheets

U.S. PATENT DOCUMENTS

| | | |
|---|---|---|
| 5,250,419 A | 10/1993 | Bernard et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,320,725 A | 6/1994 | Gregg et al. |
| 5,356,786 A | 10/1994 | Heller et al. |
| 5,462,064 A | 10/1995 | D'Angelo et al. |
| 5,593,852 A | 1/1997 | Heller et al. |
| 5,612,178 A * | 3/1997 | Gordon et al. ............... 422/56 |
| 5,624,813 A | 4/1997 | Mahant |
| 5,638,815 A | 6/1997 | Schoendorfer |
| 5,665,222 A | 9/1997 | Heller et al. |

* cited by examiner

APPARATUS FOR MONITORING A LEVEL OF A CHEMICAL SPECIES IN A BODY FLUID

FIELD OF THE INVENTION

The present invention is, in general, directed to an apparatus and method for monitoring a level of a chemical species in body fluid. More particularly, the present invention relates to a dermal apparatus and method for monitoring the level of a chemical species, such as lactate, in perspiration.

BACKGROUND OF THE INVENTION

Athletic activities typically involve the contraction and relaxation of muscles at high rates. During such activities, adenosine triphosphate (ATP) is hydrolyzed to adenosine diphosphate (ADP) producing energy for muscle contraction. The body can manufacture ATP from ADP by glucose oxidation to supply energy for continued muscular activity. When the physical or athletic activity is of low exertion, the muscles are well oxygenated and glucose is efficiently oxidized in the presence of ADP to reform ATP. As the physical or athletic performance transitions to greater intensity, oxygen becomes limited and there is a shift to anaerobic glucose oxidation for replenishing ATP. Anaerobic glucose oxidation is less efficient than aerobic oxidation producing only a fraction of ATP.

A byproduct of the anaerobic ATP manufacture is lactate, also known as lactic acid. With high intensity exercise, lactate accumulates in the muscles, for example, in the legs of runners and cyclists and in the arms of rowers. With increased accumulation of lactate, athletic performance levels decline or cease. Simultaneously, the accumulated lactate enters the bloodstream and is expelled through body secretions such as perspiration.

It is often desirable to monitor lactate levels to maximize high intensity athletic performance. By maximizing glucose oxidation efficiency an athlete can save carbohydrates, and thus perform or train longer.

A number of devices have been developed for the determination of lactate and/or other chemical species in perspiration. These devices typically include a collection pad which is attached to the skin of an individual to obtain a desired amount of perspiration. The collection pad is removed from the individual and the collected perspiration is processed to determine the amount of lactate in the perspiration using chemical or electrochemical techniques. These, however, are not practical devices for monitoring the level of lactate during exercise or other physical or athletic activities.

SUMMARY OF THE INVENTION

Generally, the present invention relates to an apparatus and method for monitoring the level of a chemical species, such as lactate or glucose, in a body fluid, such as perspiration. In particular, some embodiments of the invention permit the monitoring of the level of the chemical species during activities, such as exercise or other physical or athletic exertions. One embodiment of the invention is an apparatus for monitoring a level of a chemical species in a body fluid. The apparatus includes a fluid collection layer adapted for receiving the body fluid. The fluid collection layer is dry prior to being brought into contact with the body fluid. A catalyst is provided in, on, or near the fluid collection layer so as to be in contact with the body fluid in the fluid collection layer. The catalyst facilitates a reaction of the chemical species in the body fluid. An indicator, responsive to the reaction of the chemical species, is also provided in, on, or near the fluid collection layer. A characteristic of the indicator changes in response to the reaction of the chemical species, thereby indicating the level of the chemical species in the body fluid.

Another embodiment of the invention is an apparatus for monitoring a level of lactate in perspiration. The apparatus includes a base layer, a reaction layer, an indicator layer, and a cover layer. The base layer is adapted for placement on an animal, preferably on the skin. The reaction layer is positioned over the base layer and includes an enzyme for catalyzing a reaction of lactate in the perspiration to form a product compound. The indicator layer is positioned over the reaction layer and includes an indicator responsive to the product compound. A characteristic of the indicator, such as color, changes in the presence of the product compound. The cover layer is positioned over the indicator layer and has a window for viewing the underlying indicator layer. The reaction layer and indicator layer are dry prior to being brought into contact with the perspiration.

Yet another embodiment is an apparatus for monitoring a level of a chemical species in a body fluid. The apparatus includes a fibrous substrate adapted for collecting the body fluid, a catalyst, and an indicator. The catalyst is disposed proximate to the fibrous substrate so as to be in contact with the body fluid in the fibrous substrate to facilitate a reaction of the chemical species in the body fluid. The indicator is disposed proximate to the fibrous substrate so as to be responsive to the reaction of the chemical species. A characteristic of the indicator changes in response to the reaction of the chemical species, thereby indicating the level of the chemical species.

A further embodiment of the invention is a method for monitoring a level of a chemical species in a body fluid. A monitoring device, responsive to the chemical species, is applied to an animal, preferably on the skin. The device has an absorbent substrate, a catalyst disposed proximately to the substrate, and an indicator disposed proximately to the substrate. The absorbent substrate is dry prior to being brought into contact with the body fluid. Body fluid is received in the fibrous substrate where a chemical species in the body fluid is reacted in the presence of the catalyst. A characteristic of the indicator is then altered in response to the reaction of the chemical species.

The above summary of the present invention is not intended to describe each disclosed embodiment or every implementation of the present invention. The Figures and the detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE ILLUSTRATED EMBODIMENTS

The present invention is believed to be applicable to the monitoring of a level of a chemical species in a body fluid. In particular, the present invention is directed to an apparatus for the monitoring of a chemical species in a body fluid. One example is an apparatus to monitor lactate level in perspiration during activities, such as exercise, or other periods of physical or athletic exertion. While the present invention is not so limited, an appreciation of various aspects of the invention will be gained through a discussion of the examples provided below.

Figure 1:
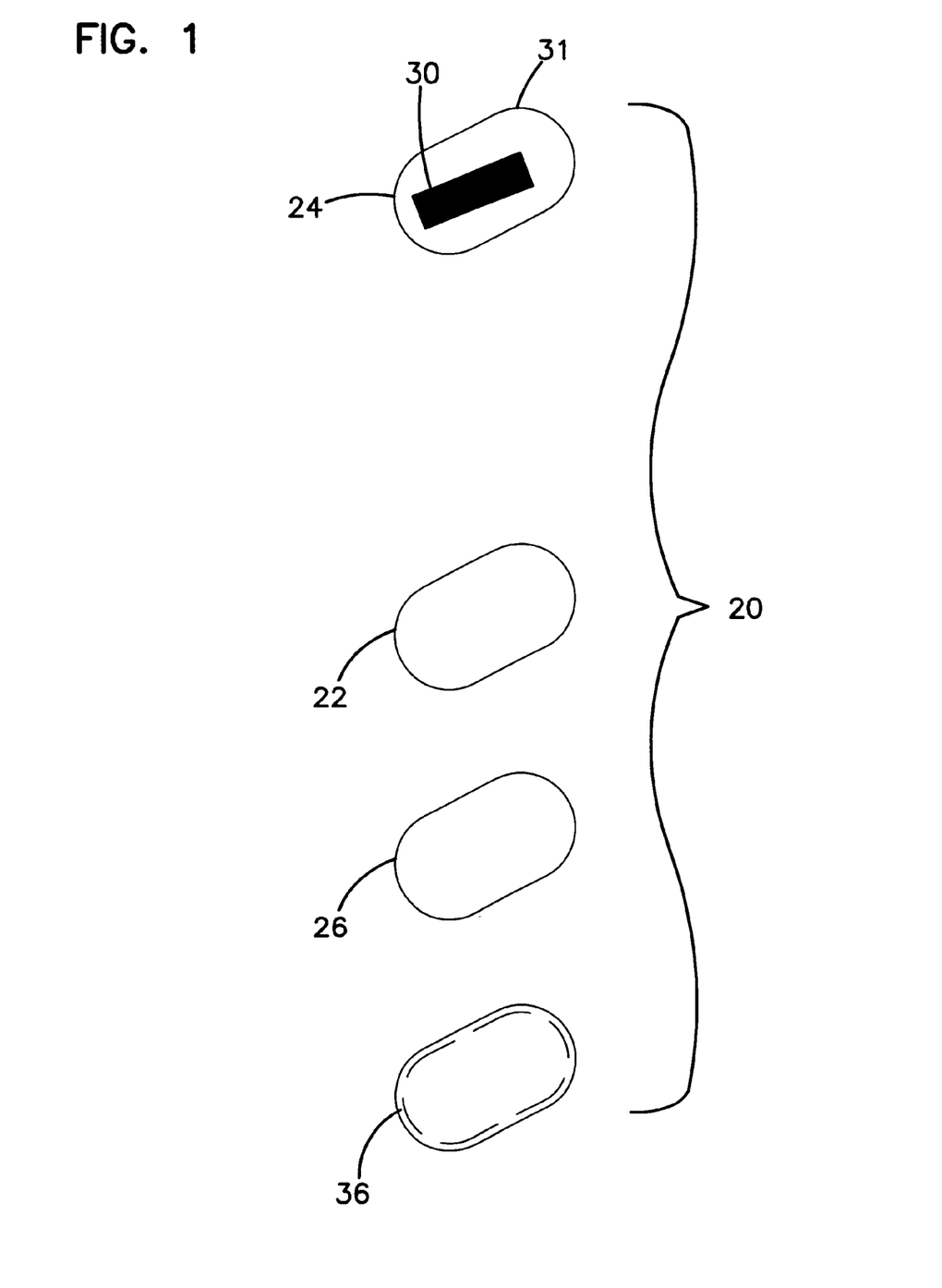
FIG. 1 is an expanded view of one embodiment, according to the invention, of an apparatus for monitoring a level of a chemical species in a body fluid.

An apparatus of the present invention have the form of, for example, a dermally applied patch 20, as illustrated in FIG. 1. However, other forms of the apparatus may also be used, such as a watch, sweat band, ring, or a decal on clothing. The dermally applied patch 20 is usually attached to the skin of a user, often at a location easily visible to the user. The patch 20 typically includes a substrate 22 containing a catalyst and an indicator. A characteristic of the indicator, such as color or luminescence, changes either directly or indirectly in response to the presence of the chemical species. The catalyst and indicator are typically disposed either in or on the substrate 22. The patch 20 may also, optionally, include a cover layer 24 and a base layer 26.

Figure 2:
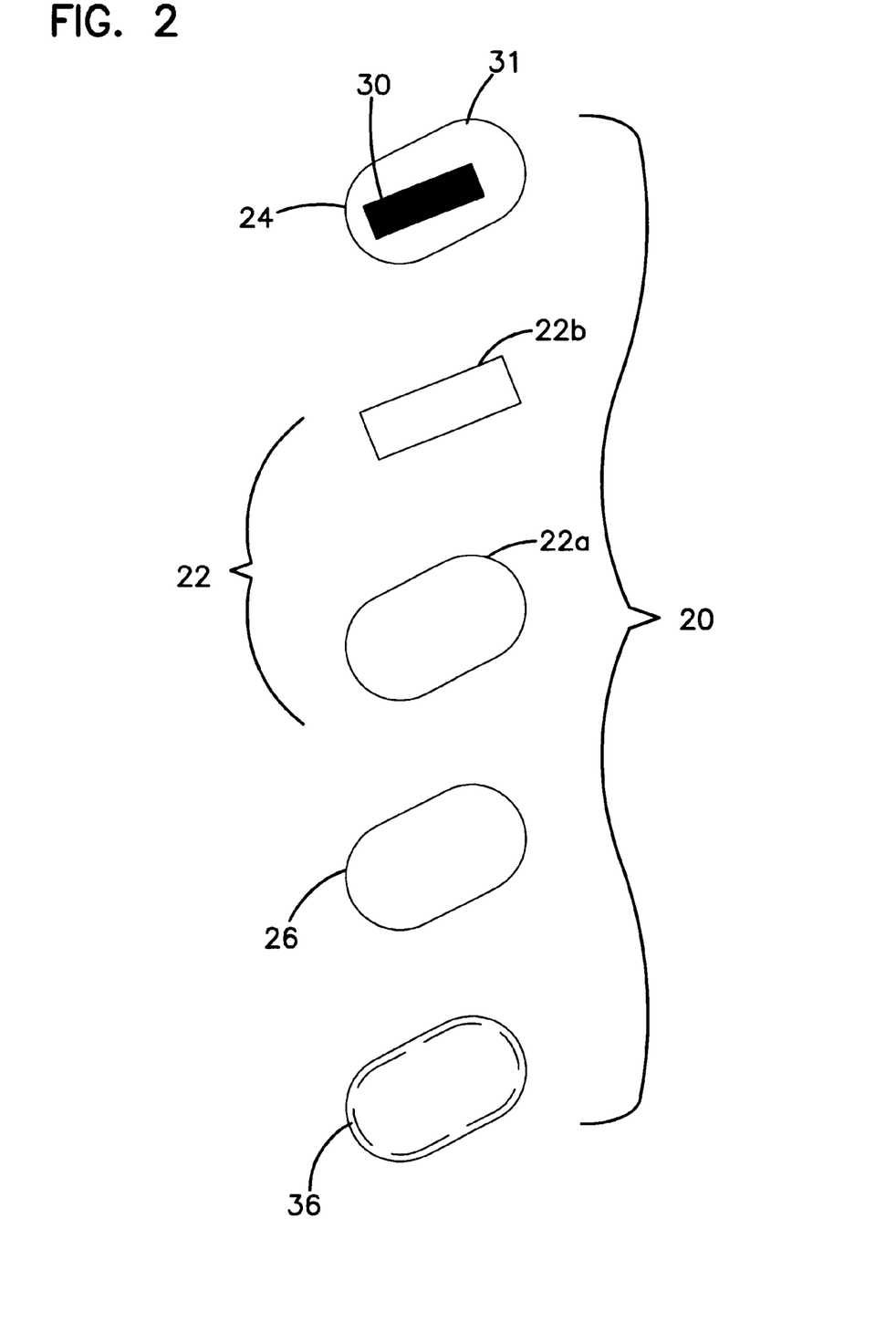
FIG. 2 is an expanded view of another embodiment, according to the invention, of an apparatus for monitoring a level of a chemical species in a body fluid.
Figure 3:
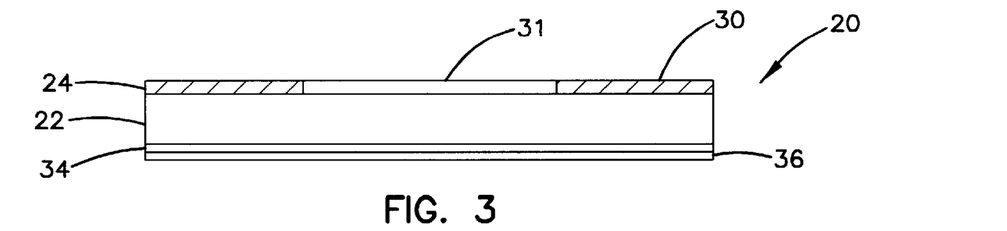
FIG. 3 is a cross-section of the apparatus of FIG. 1.
Figure 4:
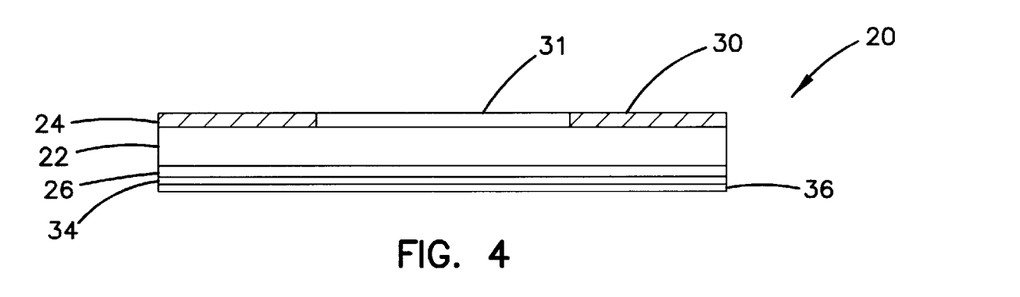
FIG. 4 is a cross-section of a further embodiment, according to the invention, of an apparatus for monitoring a level of a chemical species in a body fluid.
Figure 5:
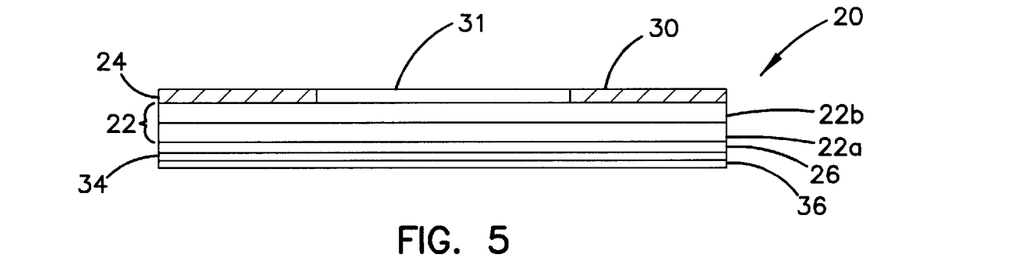
FIG. 5 is a cross-section of the apparatus of FIG. 2.

The substrate 22 may be formed using one or more sublayers. In one embodiment, the substrate 22 contains a single sublayer in which both the catalyst and the indicator reside, as shown in FIG. 3. In another embodiment, the substrate 22 has a single sublayer 22a which contains the indicator while the catalyst is deposited as a separate layer 26 on the substrate 22, as shown in FIG. 4. Well-known deposition or coating methods and techniques may be used to form layer 26 containing the catalyst. For example, the layer 26 may be formed by coating the substrate 22 with a solution containing the catalyst. The solution is then allowed to dry, forming layer 26. In yet another embodiment, the substrate 22 includes one sublayer 22a of substrate material for the catalyst and another sublayer 22b of substrate material for the indicator, as shown in FIGS. 2 and 5.

Typically, the substrate includes one or more pieces of a material which can absorb the body fluids. Examples of such substrates include fibrous materials and hydrophilic membranes. Suitable fibrous materials include, for example, paper (such as filter paper), cloth, cellulose, and hydrophilic polymer fibers. Both synthetic and natural fiber materials may be used. Preferably, the fibrous substrate contains hydrophilic fibers which may enhance the collection of the body fluid. Suitable hydrophilic membranes are made from, for example, polycarbonate, cellulose acetate, and nylon. In some embodiments, each sublayer in the substrate is formed using one or more sheets of fibrous or hydrophilic membrane material.

Typically, the patch 20 is made using materials which are dry or dried prior to the application of the patch on the user. This enhances the transfer of perspiration into the patch 20. Many previously described body fluid collection systems and analyte measurement devices for dermal application include solvents or other fluid to solvate chemical components of the systems or devices and/or to enhance osmotic flow of chemical species into the devices. However, if solvents or other fluids are used, there may be a decrease in the transport of the body fluid into the patch, as the body fluid will need to replace the fluid already in the patch 20. The patch 20 of the present invention does not rely on osmotic flow of the chemical species into the patch 20. Instead, the body fluid flows directly into the patch 20 where the level of the chemical species is tested. Thus, the patch 20 of the present invention is dry prior to application of the patch 20 to the user to enhance mass transport of the body fluid into the patch 20. In some embodiments of the patch 20, an optional cover layer 24 over the substrate 22 includes openings or is formed using a material which permits the passage of water so that the body fluid in the patch 20 may evaporate through the cover layer 24, thereby enhancing the mass transport of body fluid into the patch 20 from the skin of the user.

Another advantage of a dry patch is simplified packaging requirements and possibly longer shelf life. Devices which include fluid must provide packaging which reduces evaporation of the fluid. The evaporation rate of the fluid in these devices also determines the shelf life of these previously described devices.

The optional cover layer 24 is typically formed using a thin film of a material which covers, and may serve to protect, the underlying substrate 22. Typically, the cover layer is made using a plastic or other polymeric material, such as Teflon™, Mylar™, polycarbonate, polyethylene terephthalate, and other polyesters. In one embodiment, the cover layer 24 is made using a microporous material, such as Gore-Tex® or the like, which allows for the evaporation of at least a portion of the body fluid (e.g., water) through the cover layer 24. This may enhance the transport of the body fluid into the patch 20 as some of the body fluid evaporates and is replaced by additional body fluid.

The cover layer 24 typically has at least two regions 30, 31 of different color, as shown in FIG. 1. Often the first region 30 forms a window which is clear or translucent to allow viewing of the underlying substrate 22. The first region 30 may be colored, so long as the underlying substrate 22 is visible and any changes in the indicator in response to the presence of the chemical species are apparent. For example, if the indicator changes colors in the presence of the chemical species, either directly or indirectly, then the first region 30 is configured so that this color change is observable. This first region 30 may be formed in any shape, including simple geometrical shapes, letters, numerals, and symbols.

In some embodiments, the region 30 includes one or more openings cut in the cover layer 24 to expose the underlying substrate 22. Allowing region 30 to remain open rather than covered by a transparent or translucent material facilitates mass transport of the body fluid as the fluid evaporates through the one or more openings of the first region 30.

The second region 31 is typically formed so that it is either opaque or is of a different color than the first region 30. The second region 31 may be formed, for example, by coating or painting a portion of the cover layer 24 with an opaque material. Another technique includes forming two or more separate layers of differently colored materials which are appropriately shaped so that when they are combined, for example, by lamination or adhesive, the two or more separate layers form the first and second regions 30, 31. In some embodiments, the second region 31 is omitted (i.e., the entire underlying substrate 22 is visible).

Figure 6:
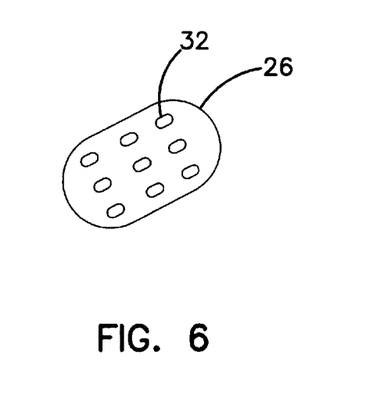
FIG. 6 is a bottom view of a base layer having openings for use in the apparatus of FIGS. 1 or 2.

An optional base layer 26 may be formed under the substrate 22. The optional base layer 26 is typically made using a thin film of a plastic or polymeric material, such as polyesters, polyethylene, polypropylene, or other similar material. One embodiment of the base layer 26 is made using a material which permits the relatively free flow of body fluid through the base layer 26. Such material may have a relatively high water permeability. In addition, openings 32 may be provided in the base layer 26, as described below. The size of the openings 32 may allow relatively free flow of body fluid through the base layer 26. These openings 32 allow the body fluid to flow into the substrate 22. Variation in the size, number, and/or density of the openings 32 may be used to restrict the flow of the body fluid into the substrate 22 and thereby permit a reduction in the amount of indicator and catalyst needed for the operation of the patch 20. The openings 32, are shown as circular in shape, but they may be of any shape, including, for example, rectangular, triangular, irregular, or combinations thereof. These openings 32 can, for example, range in dimensions (e.g., diameter, length, or width) from 2 to 5 mm, however, larger or smaller openings may also be used.

In another embodiment, the base layer 22 is made using a material, such as a Nylon®, Teflon® polycarbonate, or cellulose acetate microporous membrane, which permits a restricted flow of body fluid through the base layer 26. This particular embodiment of the base layer 26 may act as a mass transfer limiting film which may be tailored, for example, based on the material of the film, its porosity, and its thickness, to reduce the flow of the chemical species into the patch 20 by a given percentage. This may permit a reduction in the amount of indicator and catalyst needed for the operation of the patch 20.

A lower side of the base layer is optionally treated with an adhesive 34, such as a pressure sensitive adhesive (PSA), contact adhesive, or the like, as shown in FIGS. 3 to 5, to adhere the patch 20 to the skin of a user. For storage purposes, the adhesive 34 may be covered by a protective layer 36 of material, as illustrated in FIGS. 1 and 2, which may be removed from the adhesive 34 by, for example, pulling the protective layer 36 away from the adhesive when use is desired. Perforations or weakened portions may be provided on the protective layer 36, to assist in the separation of the protective layer 36 from the adhesive 34 on the patch 20.

In those embodiments in which the optional base layer 26 is not included, an adhesive 34 may be formed directly on the substrate 22 to attach the patch 20 to the skin of a user. A protective layer 36 may also be used in these embodiments to cover the adhesive 34 until use is desired.

In other embodiments, the cover layer 24 is larger than the substrate 22 and the base layer 26 and an underside of the cover layer 24 includes an adhesive, particularly along the periphery. This adhesive can be used to adhere the patch to the skin of a user and, optionally adhere the substrate 22 and/or the base layer 26 to the cover layer 24.

The patch 20 is formed by combining the one or more layers of the substrate 22 with the optional cover layer 24 and base layer 26 into a stack by, for example, bonding each of the layers together using well-known adhesive and/or lamination techniques. The layers 24, 26 and the substrate 22 may be bonded over the entire or only a portion of their surfaces (for example, around the periphery of the various layers). In some embodiments, the cover layer 24 and base layer 26 are larger than the substrate 22 or one or more layers of the substrate 22, as shown in FIG. 2. In these embodiments, the cover layer 24 and the base layer 26 may be bonded around their peripheries with the substrate 22 being held between the cover layer 24 and the base layer 26. In addition, the substrate may be bonded at one or more points to the cover layer 24 and/or the base layer 26.

The substrate 22, optional cover layer 24, and optional base layer 26 may have a variety of shapes and sizes. In some embodiments, the size of the substrate may be limited to reduce the amount of materials, such as the indicator and catalyst, that are needed to form the patch 20. However, this is not necessary constraint on the size and shape of the patch 20. Other examples of patches, include a patch in which the substrate 22, optional cover layer 24, and optional base layer 26 the same length, width, or radial dimensions, as shown in FIG. 1. As another example, the substrate 22 may be smaller than the cover layer 24 and base layer 26. In particular, the substrate 22 or one or more of the sublayers in the substrate 22 may be only slightly larger or the same size as the first region 30 (i.e., the window) in the cover layer 24, as illustrated in FIG. 2, as this is often the only portion of the substrate 22 that is viewed. This may reduce the amount of materials needed to form the patch 20.

The thickness of each of the one or more sublayers in the substrate 22 and the optional cover layer 24 and base layer 26 are typically chosen so that the patch has an overall thickness of less than about 1 to 3 mm. Typically, the one or more sublayers of the substrate 22 are chosen to each have a thickness of 300 μm or less. However, thicker patches 20 and layers of the substrate 22 may be used. The thickness of the one or more sublayers of the substrate 22 may determine the amount of body fluid that can be absorbed, as well as the amount of catalyst and indicator that are needed.

The patch 20 is formed to monitor a level of a chemical species in a body fluid. This is typically accomplished using the catalyst and the indicator provided in the patch 20. The catalyst facilitates the reaction of the chemical species to form a product compound. The indicator is then responsive to the reaction of the chemical species. For example, the indicator may respond to the presence of the product compound or a reduction in the presence of the chemical species or another reactant. The response to the reaction of the chemical species causes a change in a characteristic of the indicator, such as the color or luminescence of the indicator.

In one embodiment, the patch includes an enzyme as the catalyst. Suitable enzymes include, for example, oxidases and dehydrogenases. In addition, other enzymes and catalysts that facilitate a reaction of the chemical species and cause a response in an indicator compound may be used.

One example of a chemical species that can be monitored in this manner is lactate. It will, however, be appreciated that other chemical species which are found in perspiration, such as glucose, can be monitored using similar methods. Lactate is found in perspiration and, as described above, is indicative of the amount of muscular exertion during exercise or other physical or athletic activities. The enzyme, lactate oxidase, can be used as a catalyst to facilitate the conversion of lactate, in the presence of oxygen, to pyruvate. One product of this reaction is hydrogen peroxide. The presence and/or level of hydrogen peroxide can then be monitored using an indicator which is sensitive to hydrogen peroxide. This can then be correlated to the presence or level of lactate in the perspiration. Suitable indicators of hydrogen peroxide include, for example, a mixture of peroxidase and diaminobenzene (which changes from clear to brown in the presence of hydrogen peroxide), and a mixture of peroxidase and luminol (which luminesces in the presence of hydrogen peroxide). Commercial hydrogen peroxide test papers are available from manufacturers such as Gallard-Schlesinger (Quantofix peroxide test sticks, peroxide 100, Carle Place, N.Y., changes from white to blue in the presence of hydrogen peroxide) and EM Science (peroxide test strips, Gibbstown, N.J., changes from white to blue in the presence of hydrogen peroxide). The amount and concentration of the indicator that is used, as well as the intensity of the color change, may determine at what level of hydrogen peroxide (and, therefore, lactate) the color change of the indicator becomes noticeable. These variables may be adjusted, as well as the pore size or opening size of the base layer 26, to provide a patch 20 which has a desired response for a particular range of lactate levels.

In some embodiments, a color chart may be provided, either on the patch 20 or with the patch 20, to help the user accurately determine the level of the chemical species. In one embodiment, the second portion 31 of the cover layer 24 may be colored to coincide with a particular level of lactate. When the color of the underlying substrate 22 is the same as the second portion 31 of the cover layer 24 then that particular level of lactate has been reached.

In another embodiment of the patch 20, the enzyme, lactate dehydrogenase, facilitates the reaction of lactate and NAD$^+$(nicotinamide adenine dinucleotide) or NADP$^-$ (nicotinamide adenine dinucleotide phosphate), contained in or on the substrate 22, to form pyruvate and NADH (hydrated nicotinamide adenine dinucleotide) or NADPH (hydrated nicotinamide adenine dinucleotide), respectively. The presence and/or level of NADH or NADPH may be monitored using an appropriate indicator. Examples of suitable indicators include phenazine methylsulfate, Nile blue, pyrolloquinoline quinone (PQQ), and methylene blue. Advantages of using lactate dehydrogenase instead of lactate oxidase include the lower cost and better stability of lactate dehydrogenase.

Alternatively, NADH or NADPH may be used to generate a second product compound which is subsequently detected. For example, a reaction of NADH or NADPH with oxygen in the presence of a diaphorase enzyme forms hydrogen peroxide. The hydrogen peroxide may then be detected as described above.

Many of the indicators described above react irreversibly with the compound which they are detecting. In one embodiment, however, the substrate 22 of the patch 20 also includes a competing compound which reverses the reaction of the indicator so that the indicator is regenerated after it has been used. Typically, the rate of this regeneration reaction using the competing compound is significantly slower than the reaction of the indicator with the product compound (e.g., hydrogen peroxide), so that the indicator will remain in its altered color or luminescent state long enough to appropriately indicate the level of lactate. Preferably, regeneration of the indicator using a competing compound takes at least 1 hour, more preferably at least 3 hours, and most preferably at least 6 hours. The inclusion of the competing compound typically makes the patch 20 reusable. The number of times each patch can be used often depends on the amount of competing compound provided on the patch. Typically, the competing compound is provided in at least a 1:1 molar ratio to the indicator, preferably the ratio is at least 3:1, and more preferably at least 5:1.

In another embodiment, the indicator may be regenerated using a substance in the environment of the patch 20. For example, many indicators may be reversibly oxidized using oxygen from the atmosphere. Examples of such indicators include phenazine methylsulfate, Nile blue, PQQ, and methylene blue. The rate of regeneration may be controlled using the optional cover layer 24. For example, if the first region 30 of the optional cover layer 24 is an opening then maximum exposure to oxygen is afforded. The flow of oxygen into the patch may be slowed by use of a material in the first region 30 of the cover layer 24 which is semipermeable to oxygen. In some cases, the reaction with oxygen takes at least one hour, more preferably, at least three hours, and most preferably at least six hours. This then regenerates the patch 20 so that the patch 20 is reusable. In other cases, the regeneration of the indicator occurs on the order of minutes or seconds. Under these circumstances, the patch 20 then acts as a continuous, real-time monitor of the level of the chemical species in the body fluid.

The indicators described above are typically chromophorically active, however, other indicators may be used, including indicators which react with the product compound to produce chemiluminescence. The presence of lactate, or another chemical species, is indicated by luminescence observed through the first region 30 of the cover layer 24. One example of a chemiluminescent indicator for hydrogen peroxide is luminol (3-aminophthalohydrazide). Typically, the reaction of hydrogen peroxide and luminol requires the presence of a catalyst, such as a peroxidase enzyme, which is typically contained in or on the substrate 22.

EXAMPLES

Example 1

A two-layer patch was formed using a 2.5 cm by 1.3 cm length of clear adhesive tape (Scotch™-brand tape from 3M Co., St. Paul, Minn.). The indicator layer used in this Example was a 4 mm by 4 mm hydrogen peroxide test strip (Reflectoquant Stk# 39141, Alfa Chemicals, Ward Hill, Mass.). 10 mL of an aqueous 10 mg/mL solution of lactate oxidase (Genzyme, Cambridge, Mass., Cat. # 70-1381-01, Lot No. D60300) with 0.01 mM bicarbonate was deposited on the indicator layer. The lactate oxidase solution was rapidly dried in a vacuum chamber. After the solution was dried, the combined indicator layer was attached at the center of the clear adhesive tape.

A control test was performed by placing 20–100 μL of pH 7 phosphate buffer on the patch. This resulted in no color change.

A lactate sensing test was performed by placing 20–100 μL of an aqueous 15 mM lactate solution onto the patch. A strong change in the color, from white to blue, was observed.

A user test was performed by adhering the patch to a user's forearm using the portions of the clear adhesive tape which extended beyond the indicator layer. The user than began cycling a four mile course. After the first mile, the patch started to turn from white to blue. The color continued to darken over the four mile course.

Example 2

A three-layer patch was formed using the same clear adhesive tape and indicator layer as in Example 1. A third layer was formed by depositing 10 μL of an aqueous 10 mg/mL solution of lactate oxidase on a 5 mm by 5 mm square of Kimwipes EX-L (Kimberly-Clark Corp., Atlanta, Ga.) lab paper. After drying, the indicator layer was placed on the adhesive side of the clear adhesive tape followed by the Kirnwipe (i.e., catalyst layer). The same control, lactate sensing, and user test were performed, as in Example 1, with the same results.

Example 3

A four-layer patch was formed as shown in FIG. 1. The patch included a clear, adhesive-coated polyester cover layer (PM-200 Clear PTP Film with L-23 Adhesive, FLEXcon, Spencer, Mass.). The adhesive was coated on the back side of the cover layer. The cover layer had a width of 2.5 cm, a length of 3.8 cm, and a thickness of 50 $\mu$m. An opaque orange color was reverse printed on the front side of the cover layer except for a portion that formed a viewing window. A hydrogen peroxide test strip from Gallard-Schlesinger (Quantofix peroxide test sticks, peroxide 100, Carle Place, N.Y., changes from white to blue in the presence of hydrogen peroxide) was cut so that the test strip would cover the window in the cover layer. The test strip was then adhered to the cover layer over the window. An enzyme catalyst layer was formed by depositing 10 $\mu$L of 25 mg/mL lactate oxidase (Genzyme, Cambridge, Mass.) onto a circular piece of filter paper (Whatman Grade C-1554, Fairfield, N.J.) The enzyme layer was then adhered to the cover layer using the adhesive on the back side of the cover layer.

A base layer was formed using an adhesive-covered, 50 $\mu$m white cis-polyester film (PM-200 White Polyester TC-329 Film with Bandage Adhesive #H-566, FLEXcon, Spencer, Mass.). The adhesive was coated on a bottom surface of the base layer to adhere the base layer to the skin of the user. A 4×8 grid of 3 mm×3 mm square holes were punched in the base layer to allow the flow of perspiration into the patch. A top surface of the base layer was adhered to the cover layer using the adhesive on the cover layer. A release liner (provided with the PM-200 White Polyester TC-329 Film) covered the adhesive on the bottom surface of the base layer. The release liner was pulled away from the patch in order to adhere the patch to the skin of the user.

A control test was performed by placing 20–100 $\mu$L of pH 7 phosphate buffer on the patch. This resulted in no color change.

A lactate sensing test was performed by placing 20–100 $\mu$L of an aqueous 15 mM lactate solution onto the patch. A strong change in the color, from white to blue, was observed.

A user test was performed by removing the release liner and adhering the patch to a user's skin using the adhesive on the base layer. Users then ran a four mile course. The patch began to change color from white to blue after 1–2 miles. The color continued to darken over the four mile course.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification. The claims are intended to cover such modifications and devices.

We claim:

1. An apparatus for application to skin to monitor a level of a chemical species in a body fluid, the apparatus comprising:
    a fluid collection layer adapted for collecting the body fluid when the apparatus is applied to the skin, wherein the fluid collection layer is dry prior to being brought into contact with the body fluid;
    a catalyst disposed in contact with the fluid collection layer so as to be in contact with the body fluid in the fluid collection layer, the catalyst facilitating a reaction of the chemical species; and
    an indicator disposed in contact with the catalyst so as to be responsive to the reaction of the chemical species, wherein the indicator is selected to have a characteristic that changes in response to the reaction of the chemical species while the apparatus is applied to the skin, thereby indicating the level of the chemical species in the body fluid.

2. The apparatus of claim 1, further comprising an adhesive layer disposed on the fluid collection layer for adhering the apparatus to an animal.

3. The apparatus of claim 1, wherein the characteristic of the indicator which changes in response to the reaction of the chemical species is a color of the indicator.

4. The apparatus of claim 1, wherein the characteristic of the indicator which changes in response to the reaction of the chemical species is a luminescence of the indicator.

5. The apparatus of claim 1, wherein the fluid collection layer comprises a first sublayer in which the catalyst is disposed and a second sublayer disposed over the first sublayer and containing the indictor.

6. The apparatus of claim 1, wherein the catalyst is disposed in the fluid collection layer.

7. The apparatus of claim 1, wherein the catalyst is disposed over the fluid collection layer.

8. The apparatus of claim 1, wherein the indicator is disposed in the fluid collection layer.

9. The apparatus of claim 1, wherein the fluid collection layer comprises a fibrous substrate.

10. The apparatus of claim 1, wherein the apparatus is solvent-free prior to being brought into contact with the body fluid.

11. The apparatus of claim 1, wherein the characteristic of the indicator changes in response to a level of a product compound formed in the reaction of the chemical species.

12. The apparatus according to claim 1, wherein the catalyst covers a majority of the fluid collection layer.

13. The apparatus of claim 1, wherein the change in the characteristic is reversible.

14. The apparatus of claim 13, further comprising a competing compound in the fluid collection layer, wherein the competing compound reverses the change in the characteristic as the level of the chemical species decreases.

15. The apparatus of claim 1, further comprising a base layer adapted for placement on an animal.

16. The apparatus of claim 15, wherein an adhesive is disposed on the base layer for adhering the apparatus to the animal.

17. The apparatus of claim 15, wherein the base layer has a plurality of openings to allow body fluid through the base layer to the fluid collection layer.

18. The apparatus of claim 1, further comprising a cover layer disposed over the fluid collection layer.

19. The apparatus of claim 18, wherein the cover layer comprises a window through which the fluid collection layer is viewable.

20. The apparatus of claim 19, wherein the window is formed in the shape of a letter, numeral, or symbol.

21. The apparatus according to claim 18, wherein the cover layer is larger than the fluid collection layer and an underside of the cover layer has an adhesive, the adhesive adapted to attach the cover layer to the fluid collection layer and to attach the apparatus to the skin.

22. The apparatus of claim 1, wherein the catalyst is an enzyme.

23. The apparatus of claim 22, wherein the catalyst is an oxidase.

24. The apparatus of claim 22, wherein the catalyst is a dehydrogenase.

25. The apparatus of claim 22, further comprising a reactant compound disposed in the substrate, the reactant compound reacts with the chemical species in the presence of the enzyme to form an intermediate compound, the intermediate compound reacting to form a product compound.

26. The apparatus of claim 25, wherein the reactant compound is $NAD_+$ or $NADP_+$ and the intermediate compound is NADH or NADPH, respectively.

27. An apparatus for application to skin to monitor a level of lactate in perspiration, the apparatus comprising:
- a base layer adapted for placement on the skin of an animal,
- a reaction layer disposed on the base layer, the reaction layer comprising an enzyme for catalyzing a reaction of the lactate in the perspiration to form a product compound;
- an indicator layer disposed on the reaction layer, the indicator layer comprising an indicator responsive to the product compound, wherein the indicator is selected to change color in the presence of the product compound while the apparatus is applied to the skin of the animal; and
- a cover layer disposed over the indicator layer, the cover layer having a window for viewing the underlying indicator layer;
- wherein the reaction layer and indicator layer are dry prior to being brought into contact with the perspiration.

28. The apparatus of claim 27, wherein the reaction layer and the indicator layer form a fluid collection layer with the indicator compound and the catalyst disposed therein.

29. The apparatus according to claim 27, wherein the catalyst covers a majority of the base layer.

30. An apparatus for application to skin to monitor a level of a chemical species in a body fluid, the apparatus comprising:
- a fibrous substrate adapted for collecting the body fluid when the apparatus is applied to the skin;
- a catalyst disposed in contact with the fibrous substrate so as to be in contact with the body fluid in the fibrous substrate, the catalyst facilitating a reaction of the chemical species in the body fluid; and
- an indicator disposed in contact with the catalyst so as to be responsive to the reaction of the chemical species, wherein the indicator is selected to have a characteristic that changes in response to the reaction of the chemical species while the apparatus is applied to the skin, thereby indicating the level of the chemical species in the body fluid.

31. The apparatus according to claim 30, wherein the catalyst covers a majority of the fibrous substrate.

32. An apparatus for application to skin to monitor a level of a chemical species in a body fluid, the apparatus comprising:
- a base layer adapted for placement on an animal, said base layer adapted to allow flow of body fluid through the base layer;
- a fluid collection layer adapted for collecting the body fluid flowing through the base layer when the apparatus is applied to the skin, the fluid collection layer being positioned above the base layer;
- a catalyst layer, the catalyst being selected to facilitate the reaction of the chemical species, the catalyst layer being positioned above the fluid collection layer; and
- an indicator layer positioned above the catalyst layer, the indicator layer selected to have a characteristic that changes in response to a reaction of the chemical species while the apparatus is applied to the skin, thereby indicating the level of the chemical species in the body fluid; wherein the body fluid from the fluid collection layer must pass through the catalyst layer to reach the indicator layer.

33. The apparatus according to claim 32, wherein the fluid collection layer is absorbent.

34. The apparatus according to claim 32, wherein the catalyst layer covers a majority of the fluid collection layer.

35. The apparatus according to claim 32, wherein the characteristic of the indicator which changes in response to the reaction of the chemical species is a color of the indicator.

36. The apparatus according to claim 32, wherein the characteristic of the indicator which changes in response to the reaction of the chemical species is a luminescence of the indicator.

37. The apparatus according to claim 32, wherein the characteristic of the indicator changes in response to a level of product compound formed in the reaction of the chemical species.

38. The apparatus according to claim 32, wherein the base layer is an adhesive layer applied to the fluid collection layer.

39. The apparatus of claim 32, wherein the layers form a patch.

40. The apparatus according to claim 32, further comprising an adhesive layer applied to the base layer.

41. The apparatus according to claim 32, wherein the catalyst is an enzyme.

42. The apparatus according to claim 41, wherein the catalyst is an oxidase.

43. The apparatus according to claim 41, wherein the catalyst is a dehydrogenase.

* * * * *

UNITED STATES PATENT AND TRADEMARK OFFICE
CERTIFICATE OF CORRECTION

PATENT NO. : 6,479,015 B1  Page 1 of 1
DATED : November 12, 2002
INVENTOR(S) : Long et al.

It is certified that error appears in the above-identified patent and that said Letters Patent is hereby corrected as shown below:

Column 11,
Line 12, "compound is $NAD_+$ or $NADP_+$ and" should read -- compound is $NAD^+$ or $NADP^+$ and --

Signed and Sealed this

Tenth Day of June, 2003

JAMES E. ROGAN
*Director of the United States Patent and Trademark Office*